(12) United States Patent
Dasgupta et al.

(10) Patent No.: US 12,396,936 B2
(45) Date of Patent: Aug. 26, 2025

(54) ANTIMICROBIAL COMPOSITION FOR TACKLING MALODOUR

(71) Applicant: Conopco, Inc., Englewood Cliffs, NJ (US)

(72) Inventors: Anindya Dasgupta, Bangalore (IN); Maya Treesa Saji, Bangalore (IN); Neha Salgaonkar, Bangalore (IN)

(73) Assignee: Conopco, Inc., Hoboken, NJ (US)

( * ) Notice: Subject to any disclaimer, the term of this patent is extended or adjusted under 35 U.S.C. 154(b) by 278 days.

(21) Appl. No.: 17/923,076

(22) PCT Filed: Jun. 3, 2021

(86) PCT No.: PCT/EP2021/064942
§ 371 (c)(1),
(2) Date: Nov. 3, 2022

(87) PCT Pub. No.: WO2021/254790
PCT Pub. Date: Dec. 23, 2021

(65) Prior Publication Data
US 2023/0149274 A1    May 18, 2023

(30) Foreign Application Priority Data

Jun. 15, 2020  (IN) .............................. 202021025117

(51) Int. Cl.
| A61K 8/34 | (2006.01) |
| A61Q 15/00 | (2006.01) |
| A61Q 17/00 | (2006.01) |

(52) U.S. Cl.
CPC ................ *A61K 8/347* (2013.01); *A61K 8/34* (2013.01); *A61Q 15/00* (2013.01); *A61Q 17/005* (2013.01)

(58) Field of Classification Search
None
See application file for complete search history.

(56) References Cited

U.S. PATENT DOCUMENTS

| 4,925,655 | A | 5/1990 | Smigel et al. |
| 5,188,822 | A | 2/1993 | Viccaro et al. |
| 9,889,078 | B2 | 2/2018 | Meyer et al. |
| 10,449,137 | B2 | 10/2019 | Agarwal et al. |
| 2005/0136024 | A1 | 6/2005 | Stockel |
| 2009/0214606 | A1 | 8/2009 | Bujard et al. |
| 2011/0263526 | A1 | 10/2011 | Satyam |
| 2012/0121737 | A1 | 5/2012 | Vielhaber et al. |
| 2016/0095818 | A1 | 4/2016 | Hugerth et al. |
| 2018/0360724 | A1* | 12/2018 | Agarwal .................. C11D 3/48 |
| 2021/0145722 | A1 | 5/2021 | Siefken et al. |

FOREIGN PATENT DOCUMENTS

| CH | 497846 | 10/1970 | |
| CN | 1262614 | 8/2000 | |
| CN | 1264292 | 8/2000 | |
| CN | 103957874 | 7/2014 | |
| CN | 104414869 | 3/2015 | |
| CN | 108367050 | 8/2018 | |
| CN | 109789066 | 5/2019 | |
| CN | 110418630 | 11/2019 | |
| CO | 4230070 | 10/1995 | |
| DE | 102017212646 | 1/2019 | |
| FR | 2685638 A1 * | 7/1993 | ............ A61K 8/068 |
| GB | 744547 | 2/1956 | |
| GB | 1254369 | 11/1971 | |
| JP | 04169511 | 6/1992 | |
| JP | 11228379 | 8/1999 | |
| JP | 2011195495 | 10/2011 | |
| WO | WO9517159 | 6/1995 | |
| WO | WO9855080 | 12/1998 | |
| WO | WO9855096 | 12/1998 | |
| WO | WO2009087242 | 7/2009 | |
| WO | WO2010046238 | 4/2010 | |
| WO | WO13083393 | 6/2013 | |
| WO | WO2018001485 | 1/2018 | |
| WO | WO2018166758 | 9/2018 | |

OTHER PUBLICATIONS

FR-2685638A1—Google English Translation (Year: 1991).*
Search Report and Written Opinion in PCT/EP2021/064942; Oct. 20, 2021; World Intellectual Property Org. (WIPO).
International Preliminary Report on Patentability in PCT/EP2021/064942; Sep. 16, 2022; World Intellectual Property Org. (WIPO).
Sarengaowa et al; "Antimicrobial Mechanisms of Essential Oils and Their Components on Pathogenic Bacteria: A Review"; Food Science, vol. 41; No. 11; pp. 285-294; (2020).
Zhenyou et al; "Handbook of Skin Beauty and Cosmetic Preparations"; Publishing House of Ancient Chinese Medicine Books; $2^{nd}$ Edition; pp. 1-6; (2015).

* cited by examiner

*Primary Examiner* — Kyung S Chang
(74) *Attorney, Agent, or Firm* — Stephanie S. DelPonte

(57) ABSTRACT

The present invention relates to an antimicrobial composition, more particularly to a method and a composition to prevent or treat malodour, especially body malodor. This is achieved through a composition that comprises alkyl substituted dihydroxy benzene in combination with thymol or terpineol. The composition is also seen to have anti-acne benefits.

8 Claims, No Drawings

ANTIMICROBIAL COMPOSITION FOR TACKLING MALODOUR

FIELD OF THE INVENTION

The present invention relates to an antimicrobial composition, more particularly to a method and a composition to prevent or treat malodour, especially present in human axilla. The composition is also seen to have anti-acne benefits.

BACKGROUND OF THE INVENTION

In humans, the skin of underarm provides a unique niche for bacteria. Through the secretions of various glands that open onto skin, the environment is nutrient rich and hosts a unique microbial community. In humans, the link between axillary apocrine gland secretions, underarm bacteria and body odour have been long established. Culture-based studies on this relationship found the axillary microbiota to be dominated by *Staphylococcus, Corynebacterium* and *Propionibacterium* species. More recent culture-independent studies have confirmed the presence of these genera and additionally, indicated the presence of Gram-positive anaerobic cocci (GPAC) belonging to *Anaerococcus* and *Peptoniphilus* genera. The primary reason for these studies was to identify target bacterial species responsible for axillary malodour and thereby design strategies to control it for providing the axillary malodour reduction benefit.

Human body odour contains several chemicals, but the most pungent and recognizable are thioalcohols. These molecules are created through a series of chemical reactions that start with an odourless precursor; a compound produced in glands located in the armpits. Popular theory has it that a type of bacteria called *Staphylococcus hominis* (*S. hominis*) takes in these molecules and transforms them into thioalcohols which give the body the malodour.

Body malodour has been tackled in many ways. Some of these approaches are use of perfumes to mask the malodour but this approach has benefit only for a limited time. Anti-perspirant compositions are also available but they block the sweat glands thereby depriving the body of a mechanism to excrete undesirable chemicals through sweat.

The present inventors in seeking to solve the problem of malodour worked towards methods for controlling the bacterial population in the underarm region. It is possible to completely eradicate or minimize all the bacteria on the skin through the use of agents like alcohol.

However, the present inventors wish to use more natural agents which are less harsh on skin.

The present inventors thus started working towards providing "natural" solutions to solving the problem of malodour. They finally hit upon a combination of specific alkyl substituted dihydroxy benzene and compounds like thymol and/ or terpineol which interact synergistically to provide the desired malodour reduction benefit.

WO9517159 (P&G, 1995) discloses a concentrated mouth rinse for efficient delivery of antimicrobials which comprises a combination of cationic antimicrobials, non-cationic antimicrobials and flavouring agent to provide anti-plaque benefits. Although such a composition has been shown to provide antibacterial benefits with the non-cationic antibacterial selected from hexyl resorcinol or thymol along with various other such agents, it does not disclose that such a composition is effective against underarm odour causing bacteria like *S. hominis*.

The inventors then further found that this composition is also effective in tackling acne. Acne, also known as Acne vulgaris, is a common skin condition that affects nearly all adolescents and adults at some point in their lives. It has a complex etiology, involving abnormal keratinization, excess sebum production, androgen function, bacterial growth, and immune hypersensitivity. Although one or more of the above processes is correlated with acne, the one triggering factor and the exact sequence of events leading to the formation of acne lesions has not been fully understood. Other factors which have been linked to acne are presence of free radicals with subsequent oxidative stress leading to cellular damage. It has been observed that acne usually occurs in areas rich in sebaceous glands like the face, neck and back.

A bacteria *Cutibacterium acnes* (*C. acnes*) formerly *Propionibacterium acnes* has also been implicated in occurrence of acne. It is one of the important and dominant bacteria residing on the human facial skin surface. *C. acnes* is an aerotolerant anaerobe, slow-growing, rod shaped Gram-positive bacteria. It resides in the sebaceous glands and it constitutes an important part of the skin commensal microbiota. *C. acnes* uses sebum and by-product from surrounding skin tissue as sources of energy and nutrients. This results in some fatty acid release which can irritate the follicle wall and induce inflammation, leading to acne or acne vulgaris. Acne vulgaris is a chronic, inflammatory disorder of the pilosebaceous gland. It affects almost all adolescents at some point of their lives with 15 to 20% suffering from moderate to severe forms of acne.

Acne has been treated in many ways. Most treatments take several weeks to months before a noticeable change is seen. Benzoyl peroxide which has an antibacterial effect has been used for mild cases of comedones. In very severe cases of acne, antibiotics like tetracycline, erythromycin and clindamycin have been used. Antibiotics are believed to work by several mechanisms, the most important being the decrease in the number of bacteria in and around the follicle. They are also thought to reduce the irritating chemicals produced by the white blood cells in the sebum, thereby reducing the inflammatory response. However, the drawback of antibiotics and other sort of general antimicrobial treatment is that they are broad-spectrum and help in killing or inhibiting most of the bacteria on skin.

Most of the treatments, as summarized above, involve use of synthetic chemicals. Of late, more and more people prefer use of materials which are "natural" or nature identical. In this respect also, the present invention involving a combination of e.g. a resorcinol derivative and an essential oil selected from thymol or terpineol provides for a more natural method of tackling or alleviating the problem of acne.

It is thus an object of the present invention to provide for an antimicrobial composition to tackle body malodour.

It is another object of the present invention to provide for tackling bodily malodour while also ensuring prevention or reduction of occurrence of acne.

SUMMARY OF THE INVENTION

The first aspect of the present invention relates to an antimicrobial composition comprising:
(i) alkyl substituted dihydroxy benzene wherein the alkyl group comprises 2 to 10 carbon atoms;
(ii) an essential oil compound selected from thymol or terpineol; and,
(iii) a cosmetically acceptable base.

Another aspect of the present invention relates to a composition according to the first aspect for providing malodour reduction to skin on application of the composition of the first aspect to a desired skin surface.

Yet another aspect of the present invention relates to a composition according to the first aspect for providing anti acne benefit to skin on application of the composition of the first aspect -to a desired skin surface.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated.

Except in the operating and comparative examples, or where otherwise explicitly indicated, all numbers in this description indicating amounts of material or conditions of reaction, physical properties of materials and/or use are to be understood as modified by the word "about". Unless specified otherwise, numerical ranges expressed in the format "from x to y" are understood to include x and y. When for a specific feature multiple preferred ranges are described in the format "from x to y", it is understood that all ranges combining the different endpoints are also contemplated.

The composition as per this invention could be in the form of a leave-on or wash-off format for delivering selective malodour benefit to topical areas e.g. skin and/or hair of mammals, especially humans. Such a composition includes any product applied to a human body for also improving appearance, cleansing, or general aesthetics. The composition of the present invention may be delivered with a topically/cosmetically acceptable base which could be an anhydrous base, liquid, lotion, cream, foam, scrub, gel, emulsion or a propellant. "Skin" as used herein is meant to include skin on any part of the body (e.g., neck, chest, back, arms, underarms, hands, legs, buttocks and scalp) especially the underarm. It is especially useful for reduction of malodour from the underarm (or axilla) or any other part of the body where malodour is generated. For the desired anti-acne benefit the composition of the invention could be applied to any part of the body which is generally seen to be afflicted with acne. Such surfaces include the face or any other part of the body where acne forms.

The antimicrobial composition of the invention comprises alkyl substituted dihydroxy benzene wherein the alkyl group comprises 2 to 10 carbon atoms; an essential oil compound selected from thymol or terpineol; and a cosmetically acceptable base.

Alkyl substituted dihydroxy benzene has the general chemical structure (I) as given below:

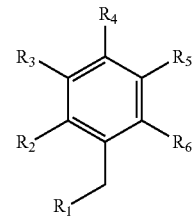

(1)

Wherein $R_1$ is $C_1$ to $C_{10}$ alkyl group; and each of $R_2$ to $R_6$ is either an OH group or H; and
wherein at least two of $R_2$ to $R_6$ is OH. $R_1$ is $C_2$ to $C_{10}$ alkyl group.

Structure of more preferred alkyl substituted dihydroxy benzene for use in the present invention is

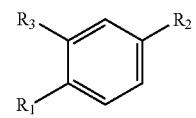

Wherein $R_1$ is a $C_1$ to $C_{10}$ alkyl group; $R_2$ and $R_3$ are OH. $R_1$ is $C_2$ to $C_{10}$ alkyl group.

Preferably $R_1$ is an alkyl group comprising 2 to 10 carbon atoms, preferably comprising 2 to 6 carbon atoms, most preferably comprising 2, 4 or 6 carbon atoms. The two hydroxy groups are generally at the 1 and 3 position. Such compounds are often referred to as substituted resorcinols. Thus, the most preferred compounds are ethyl resorcinol, butyl resorcinol or hexyl resorcinol. The 4-substituted resorcinol is most preferred. Thus, the resorcinols which may be used are 4-ethyl resorcinol, 4-butyl resorcinol or 4-hexyl resorcinol. The most preferred compound for use in the present invention is 4-hexyl resorcinol. This compound has the structure given below:

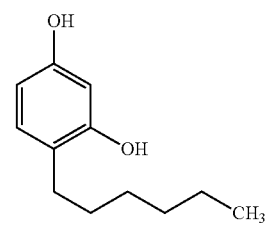

The compound is also known by its synonyms 4-hexyl-benzene-1,3-diol, and 4-hexyl-1,3-benzenediol.

Hexylresorcinol is known to exhibit antiseptic and local anaesthetic properties. It has been used in topical applications for minor skin infections and in oral solutions for pain relief and as a first aid antiseptic. It has also been used as a skin-glow agent in skin care. The compound is also known to have antioxidant properties and so have been used in skin care compositions to provide skin with an even tone complexion or in anti-aging products.

The composition preferably comprises 0.0005% to 10% alkyl substituted dihydroxy benzene by weight of the composition. It is more preferably present in an amount ranging from 0.001 wt. % to 2 wt. % of the composition.

The composition of the invention preferably comprises either thymol or terpineol.

The structure of thymol is given below:

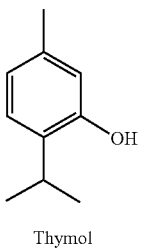

Thymol

Alternately the composition may comprise terpineol. The terpineol is preferably selected from alpha-terpineol, beta-terpineol, gamma-terpineol or mixtures thereof. It is particularly preferred that the terpineol is alpha-terpineol.

The structure of a terpineol compound is given below:

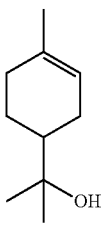

The compounds thymol and terpineol are both in the class of essential oil compound. They are both known to have strong odour and are therefore used in perfumery compositions. They are both also known to have antimicrobial activity. They may be extracted from herbs found in nature or may be synthetically prepared and used in the present invention. In the present invention both are used from synthetic sources. The essential oil compound is included in 0.001% to 5%, preferably 0.005% to 1%, furthermore preferably 0.005% to 0.5% by weight of the composition.

As per an especially preferred aspect of the invention, the composition comprises a mixture of thymol and terpineol. Other essential oil compounds which may optionally be included in the composition of the invention are carvacol, (E)-2(prop-1-enyl) phenol, 2-propylphenol, 4-pentylphenol, 4-sec-butylphenol, 2-benzyl phenol, eugenol or combinations thereof.

Without wishing to be bound by theory, the present inventors believe that the combination of the actives claimed in the present invention works due to the following reason. Alkyl substituted dihydroxy benzene, example Hexyl resorcinol, interacts with the biological membranes and intracellular proteins of bacteria. Due to its amphiphilic nature it penetrates the bacterial cell to damage the integrity of the membrane and increase permeability. Once inside the cell it possibly acts on multiple targets and kills the bacteria. The essential oil compound e.g. thymol, a monoterpenoid is a fast-acting antimicrobial that destabilizes the bacterial membranes. Together we see a synergy with Alkyl substituted dihydroxy benzene (e.g. hexyl resorcinol) and the essential oil compound e.g. thymol in our assays. We hypothesize that the fast acting ability of thymol aids in penetration of hexyl resorcinol and thus in combination it acts as a potent and fast acting synergistic antimicrobial combination.

The composition of the invention comprises a cosmetically acceptable base. The cosmetically acceptable base preferably comprises a gel, emulsion, lotion, paste, spray, or cream. In the above formats, the cosmetically acceptable base preferably comprises water, surfactant or combinations thereof. The surfactant is preferably an anionic surfactant, preferably soap.

An especially preferred form of the composition of the invention involves a cosmetically acceptable base which is anhydrous. Such anhydrous compositions are useful for deodorant products especially for application in the under-arm region.

Such compositions are generally delivered in a stick form, or from a roll-on device or delivered from an aerosol can or as a spray.

The composition may also be delivered in the form of a sanitizer comprising more than 60% ethanol by weight of the composition.

The composition comprises a topically/cosmetically acceptable base which is preferably anhydrous. By an anhydrous base is meant that water content in the composition is less than 5 wt. %, preferably less than 2 wt. %, more preferably less than 1 wt. % and optimally absent from the composition. To enable this, the anhydrous base preferably comprises a silicone compound, an alcohol or a wax. The alcohol, when used, could be a low boiling ($C_2$ to $C_4$) alcohol or a polyhydric alcohol, preferably a polyhydric alcohol.

The pH of the composition is preferably higher than 3.5 more preferably in the range of 4 to 7. The pH of the composition of the invention is measured using the following procedure: Equal volumes of the composition and model ionic sweat (pH 6.1) are mixed, and the pH value is measured using an accurate range pH test paper.

The anhydrous composition of the invention preferably comprises a polyhydric alcohol. Polyhydric alcohol is also referred to in short as polyol. A polyhydric alcohol as per the present invention is a compound having two or more hydroxyl groups. Suitable class of polyhydric alcohols that may be included in the composition of the invention are monomeric polyols, polyalkylene glycols or sugars. Preferred monomeric polyols are glycol; alkylene glycol e.g. propylene glycol; glycerol; or xylitol, more preferably propylene glycol.

Suitable polyalkylene glycols are polyethylene glycol or polypropylene glycol. Sugars for inclusion in the invention could be monomeric, dimeric, trimeric or of the polymeric form. Preferred sugars include glucose, fructose, mannose, sucrose, threitol, erythritol, sorbitol, mannitol, galactitol, adonitol, dextran, or cyclodextrin. Of these the more preferred sugars are glucose, fructose, sucrose, sorbitol, mannitol, adonitol, dextran, or cyclodextrin.

Other components commonly included in conventional compositions may also be incorporated in the composition of the present invention. Such components include skin care agents such as emollients, humectants and skin barrier promoters; skin appearance modifiers such as skin glow agents and skin smoothing agents; anti-microbial agents, in particular organic anti-microbial agents, and preservatives.

The composition of the invention can be applied cosmetically and topically to the skin, broadly speaking, by one of two methods. Some consumers prefer one method and some others, the other method. In one method, sometimes called a contact method, a composition is wiped across the surface of the skin, depositing a fraction of the composition as it passes. In the second method, sometimes called the non-contact method, the composition is sprayed from a dispenser held proximate to the skin, often in an area of about 10 to 20 $cm^2$. The spray can be developed by mechanical means of generating pressure on the contents of the dispenser, such as a pump or a squeezable sidewall or by internally generated pressure arising from a fraction of a liquefied propellant volatilizing, the dispenser commonly being called an aerosol.

There are broadly speaking two classes of contact compositions, one of which is liquid and usually applied using a roll-on dispenser or possibly absorbed into or onto a wipe, and in the second of which the antiperspirant active is distributed within a carrier liquid that forms a continuous phase that has been gelled. In one variation, the carrier fluid comprises a solvent for the antiperspirant and in a second variation, the antiperspirant remains a particulate solid that is suspended in an oil, usually a blend of oils.

Stick or Soft Solid Compositions

Many different materials have been proposed as gellant for a continuous oil phase, including waxes, small molecule gelling agents and polymers. They each have their advantages and of them, one of the most popular class of gellant comprises waxes, partly at least due to their ready availability and ease of processing, including in particular linear fatty alcohol wax gellants. A gelled antiperspirant composition is applied topically to skin by wiping it across and in contact with the skin, thereby depositing on the skin a thin film.

The nature of the film depends to a significant extent on the gellant that is employed. Although wax fatty alcohols have been employed as gellant for many years, and are effective for the purpose of gelling, the resultant product is rather ineffective at improving the visual appearance of skin, and in particular underarm skin, to which the composition has been applied. This problem has been solved by including ameliorating materials for example, di or polyhydric humectants and/or a triglyceride oil.

Roll-On

Liquid compositions that are applicable from a roll-on broadly speaking can be divided into two classes, namely those in which an antiperspirant active is suspended in a hydrophobic carrier, such as a volatile silicone and those in which the antiperspirant active is dissolved in a carrier liquid. The latter has proven to be more popular. There are mainly two sorts of dissolving carrier liquid, namely carriers that are predominantly alcoholic, which is to say the greater part of the dissolving carrier fluid comprises ethanol and the second class in which the carrier liquid is mainly water. The former was very popular because ethanol is a mild bactericide in its own right, but its popularity waned because it stings, especially if the surface onto which the composition has been applied has been damaged or cut, such as can easily arise during shaving or other de-hairing operations.

The second class of formulations that is an alternative to alcoholic formulations comprise a dispersion of water-insoluble or very poorly water soluble ingredients in an aqueous solution of the antiperspirant. Herein, such compositions will be called emulsions. Antiperspirant roll-on emulsions commonly comprise one or more emulsifiers to maintain a distribution of the water-soluble ingredients.

Aerosol Compositions

The composition of the invention may be delivered through an aerosol composition which comprises a propellant in addition to the other ingredients described hereinabove. Commonly, the propellant is employed in a weight ratio to the base formulation of from 95:5 to 5:95. Depending on the propellant, in such aerosol compositions the ratio of propellant to base formulation is normally at least 20:80, generally at least 30:70, particularly at least 40:60, and in many formulations, the weight ratio is from 90:10 to 50:50. A ratio range of from 70:30 to 90:10 is sometimes preferred.

Propellants herein generally are one of three classes; i) low boiling point gasses liquifided by compression, ii) volatile ethers and iii) compressed non-oxidising gases.

Class i) is conveniently a low boiling point material, typically boiling below −5° C., and often below −15° C., and in particular, alkanes and/or halogenated hydrocarbons. This class of propellant is usually liquefied at the pressure in the aerosol canister and evaporates to generate the pressure to expel the composition out of the canister. Examples of suitable alkanes include particularly propane, butane or isobutane. The second class of propellant comprises a very volatile ether of which the most widely employed ether hitherto is dimethyl ether. This propellant can advantageously be employed at relatively low weight ratio of propellant to base formulation, for example to as low as 5:95. It can also be employed in admixture with, for example, compressible/liquefiable alkane gasses. The third class of propellant comprises compressed non-oxidising gasses, and in particular carbon dioxide or nitrogen. Inert gases like neon are a theoretical alternative.

When the composition of the invention is delivered in a roll-on, a firm solid or a stick format, the topically acceptable base comprises a hydrophobic carrier or an aqueous carrier. The hydrophobic carrier in such cases may comprise a silicone compound, low boiling alcohol or a wax. When the composition comprises a propellant it is delivered as an aerosol.

The composition of the invention preferably additionally comprises a fragrance. By a fragrance is meant a molecule or a composition comprising a group of molecules that produces a pleasant odour. The composition preferably comprises a fragrance in 0.1 to 3% by weight of the composition.

Skin Care Composition

The composition of the present invention may be used for skin care. The cosmetically acceptable base in such cases may be a liquid or solid material. Typically, cosmetically acceptable base is present in an amount ranging from 10 to 99.9%, more preferably from 20 to 95%, most preferably from 40 to 85% by total weight of the composition including all ranges subsumed therein.

It is particularly preferred that the cosmetically acceptable carrier includes water. Water is preferably included in an amount from 30 to 90%, more preferably from 30 to 85%, most preferably from 30 to 80% by total weight of the sunscreen composition. Besides water, suitable carrier classes include silicones, polyhydric alcohols, hydrocarbons, triglycerides and thickening powders.

The cosmetically acceptable bases preferably delivered in a water containing format includes for e.g. a gel, cream, lotion or emulsion format. The skin care composition of the invention may be in any form including toners, lotions, creams, mousses, scrub, serum or gel that is suitable for topical application to the skin. The composition can be either a leave-on product such as skin lotions, creams, lipsticks, foundations, mascara, sunless tanners and sunscreen lotions or a rinse-off product such as shower gels and toilet bars. It is preferred that the composition is a skin lotion or a cream.

One such format is where the water containing product is thickened through use of thickeners to form a gel. An oil in water emulsion, either in lotion or in cream format, is where composition preferably comprises fatty acid. Lotions generally contain 3 to 8 wt. % fatty acid. $C_{12}$ to $C_{20}$ fatty acids are especially preferred, furthermore preferred being $C_{14}$ to $C_{18}$ fatty acids. The fatty acid is preferably substantially (generally about 90 to 95%) a mixture of stearic acid and palmitic acid. A mixture of stearic acid and palmitic acid in weight ratio of 55:45 is known as hysteric acid.

Preferably, the composition of the invention is delivered in the form of a vanishing cream. A vanishing cream is one which when applied and rubbed on to the human skin, vanishes on the skin leaving behind no significant streaks of the composition. Fatty acids when present in a composition along with a soap provides the so-called vanishing cream effect. Preferably, the leave-on composition comprises fatty acids having 10 to 30, more preferably 12 to 25, even more preferably 14 to 20, further more preferably 16 to 18 carbon atoms. Examples of fatty acids that may be used in the composition include pelargonic, lauric, myristic, palmitic, stearic, isostearic, oleic, linoleic, arachidic, behenic, erucic acid and mixtures thereof. Preferably, the fatty acid that may be used is stearic acid or palmitic acid or a mixture thereof. The fatty acid in the present invention is preferably hysteric acid which is substantially (generally about 90 to 95%) a mixture of stearic acid and palmitic acid in a ratio of between 55:45 to 45:55.

Preferably, the composition comprises from 2.25 to 25 wt %, more preferably from 4 to 22 wt %, even more preferably from 6 to 20 wt %, furthermore preferably from 8 to 19 wt % and still more preferably from 10 to 18 wt % and yet more preferably from 12 to 16 wt % fatty acid.

Preferably, the composition comprises soap. Soap, when present in combination with fatty acid in the composition, provides the vanishing effect described above. Preferably, soap in the composition is generally prepared by in-situ neutralization of fatty acid that may be present in the composition. Thus, it is preferred that the soap has a carbon chain length that corresponds to the chain length of fatty acid in the composition. The soap is formed from the fatty acid through use of alkali metal hydroxides e.g. sodium hydroxide or potassium hydroxide. Of the two, potassium hydroxide is more preferred. Thus, the soap is preferably a potassium soap (potassium salt of fatty acid).

Preferably, the composition comprises from 0.1 to 10 wt %, more preferably from 0.25% to 8 wt %, even more preferably from 0.5 to 7 wt %, further more preferably from 0.5 to 5 wt % soap, even further more preferably 0.5% to 3%.

The composition may comprise an emollient oil that act as a co-solvent. Suitable emollient oils include, for example, ester of alkoxylated aromatic alcohol with fatty carboxylic acid, esters of polyglycols or diols with fatty carboxylic acid such as caprylic/capric triglyceride, ester of fatty alcohol and fatty acid, alkoxylated derivative of benzyl alcohol and mixtures thereof. Preferably the emollient oil is caprylic/capric triglyceride.

Typically, such compositions comprise co-solvent in an amount from 0.01 to 10%, more preferably from 0.1 to 8%, most preferably from 1 to 6%, based on the total weight of the sunscreen composition and including all ranges subsumed therein.

Creams are where the compositions generally comprise 8 to 24 wt % fatty acid. Part of the fatty acid may be neutralized to form soap which may be present in 1 to 10% by weight of the composition. Such cosmetically acceptable base is usually from 10 to 99.9%, preferably from 50 to 99% by weight of the composition. The cosmetically acceptable base preferably includes water. Water is preferably included in 35 to 90%, more preferably 50 to 85%, furthermore preferably 50 to 80% by weight of the composition.

A water-in-oil emulsion may also be included as the cosmetically acceptable base. The cosmetically acceptable base in such emulsions generally comprises 5-50% silicone elastomer, preferably 10 to 30% by weight of the base. Silicone elastomer is preferably present in 1 to 15% by weight of the composition.

Silicone elastomers differ from linear polymers because of cross-linking. Many silicone elastomers are made from linear silicone polymers that contain reactive sites along the polymer chain. Elastomers have very different physical and chemical properties from linear polymers, and the properties of elastomers depend very much on the number of cross-links. An elastomer with a relatively small number of cross-links will be very soft and will swell significantly in the presence of a compatible solvent. As the number of cross-links increases, the hardness of the elastomer increases, and the elastomer will swell to a lesser extent in the presence of solvent. A highly suitable silicone elastomers for use in the composition of the invention is DC 9045, a dimethicone crosspolymer commercially available from Dow Corning. DC 9045 is chemically a blend of cyclopentasiloxane swelling agent and dimethicone crosspolymer (12-13%).

The swelling agent is most preferably a silicone fluid or a functional silicone fluid. The swelling agent is preferably used in an amount which is in a weight ratio of 1:10 to 10:1, more preferably 1:1 to 5:1 with respect to the reaction mixture where the silicone elastomer is prepared. Swelling agent is most preferably low molecular weight silicone oil which includes (i) low molecular weight linear and cyclic volatile methyl siloxanes, (ii) low molecular weight linear and cyclic volatile and non-volatile alkyl and aryl siloxanes, and (iii) low molecular weight linear and cyclic functional siloxanes. Most preferred, however, are low molecular weight linear and cyclic volatile methyl siloxanes (VMS). By "low molecular weight" in this paragraph is meant a compound having a molecular weight from 1000 to 9000.

Other useful silicone elastomer blends which may be used in the present invention are commercially available as (i) DC 9027 (a blend of an ultra-high viscosity dimethiconol and silicone elastomer in cyclopentasiloxane) available from Dow Corning; (ii) DC 9546 (a blend of high molecular weight silicone elastomer, cyclopentasiloxane and a high molecular weight linear silicone polymer) available from Dow Corning, (iii) EL8050 (a blend of high molecular weight polyglycol-modified silicone elastomer in isododecane) available from Dow Corning and (iv) EL8051 (a blend of high molecular weight polyglycol-modified silicone elastomer in isodecyl neopentanoate) available from Dow Corning.

Such water in oil emulsion composition preferably comprises 10 to 70%, more preferably 30 to 50% water by weight of the composition.

Useful sun-protective agents e.g. inorganic sunscreen may be preferably used in the present invention. These include, for example, zinc oxide iron oxide, silica, such as fumed silica, or titanium dioxide. The total amount of inorganic sunscreen that is preferably incorporated in the composition according to the invention is from 1 to 8%, preferably 3 to 8% by weight of the composition. It has been observed that inclusion of inorganic sunscreen provides further synergistic benefit in SPF in addition to the essential ingredients of the present invention. The composition of the invention may comprise a UV-A sunscreen agent selected from the group consisting of a dibenzoylmethane derivative, a triazine derivative, a benzophenone derivative and mixtures thereof. In a preferred embodiment, the UV-A sunscreen agent comprises or is a dibenzoylmethane derivative, for example, butyl methoxydibenzoylmethane (sold under the trade name Parsol 1789).

Typically, the sunscreen composition of the present invention comprises from 0.1 to 15% by weight of the UV-A sunscreen agent, more preferably from 0.1 to 10%, most preferably from 1 to 5%, based on the total weight of the composition and including all ranges subsumed therein.

The composition of the invention may also comprise a UV-B sunscreen agent. Suitable UV-B sunscreen agent of the invention is selected from the group consisting of a benzophenone, an anthranilate, a salicylate, a cinnamate, a camphor, benzylidene malonate, a triazone, and derivatives thereof. In a preferred embodiment, the UV-B sunscreen agent comprises or is a cinnamate derivative, for example, ethylhexyl methoxycinnamate (sold under the trade name Parsol MCX).

Typically, the composition comprises from 0.1 to 20% by weight of the UV-B sunscreen agent, more preferably from 0.5 to 18%, most preferably from 1 to 15%, based on the total weight of the composition and including all ranges subsumed therein.

The composition of the invention may additionally comprise a skin glow agent. The skin glow agent is preferably chosen from a vitamin B3 compound or its derivative e.g. niacin, nicotinic acid, niacinamide or other well-known skin glow agents e.g. aloe extract, ammonium lactate, azelaic acid, kojic acid, citrate esters, ellagic acid, glycolic acid, green tea extract, hydroquinone, lemon extract, linoleic acid, magnesium ascorbyl phosphate, vitamins like vitamin B6, vitamin B12, vitamin C, vitamin A, a dicarboxylic acid, resorcinol derivatives, hydroxycarboxylic acid like lactic acid and their salts e.g. sodium lactate, and mixtures thereof. Vitamin B3 compound or its derivative e.g. niacin, nicotinic acid, niacinamide are the more preferred skin glow agent as per the invention, most preferred being niacinamide. Niacinamide, when used, is preferably present in an amount in the range of 0.1 to 10%, more preferably 0.2 to 5% by weight of the composition.

The composition according to the invention may also comprise other diluents. The diluents act as a dispersant or carrier for other materials present in the composition, so as to facilitate their distribution when the composition is applied to the skin. Diluents other than water can include liquid or solid emollients, solvents, humectants, thickeners and powders.

The compositions of the present invention can comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

Another aspect of the present invention relates to a composition according to the first aspect for providing malodour reduction to skin on application of the composition to a desired skin surface. The method is preferably non-therapeutic.

According to yet another aspect, disclosed is a composition according to the first aspect for providing anti acne benefit to skin on application of the composition of the invention onto the desired skin surface.

The invention will now be illustrated with the help of the following non-limiting examples:

EXAMPLES

Examples A-D,1: Effect of Various Actives and Combination of Actives on Malodour as Measured Using Malodour Reduction Assay The actives as shown in Table—1 below were subjected to malodour reduction assay as described below:
Malodour assay using Lead acetate method:
Preparation of Bacterial Culture:

*S. hominis* is the key bacteria responsible for thiol mediated body malodour and hence the test organism used in this study was *S. hominis* ATCC 27844. The test organisms was grown on TSA (Tryptic Soya Agar) plates overnight (22±2 hr). The organism was not more than 3 passages removed from the original source. The cell number was adjusted by re-suspending it in a suitable amount of physiological saline sufficient to achieve the required cell number based on optical density of the cells. The optical density (OD at 620 nM) of the cells were standardized to the cell number for the test organism using a spectrophotometer. A minimum final suspension of $1.0 \times 10^8$ CFU/mL was achieved by adjusting the OD to 0.2 in saline for the malodour assay.
Preparation of Lead Acetate Paper:

A 1% Lead acetate solution was made in distilled water. Whatmann filter paper (cut in the size that could be placed over the wells of a well plate) was dipped in the lead acetate solution. The excess solution was drained and allowed to dry in Laminar Air Flow for 30 minutes.
Preparation of Actives Stocks:

Stock solutions of the actives were prepared for performing the assay. A 1:1 mix of thymol and terpineol was prepared by weighing equal amounts of both the materials (10 g of each) and mixing it under magnetic stirrer for 4 to 5 hours. A 0.5% stock of this mix was then prepared in ethanol by weighing 0.5 grams of mix and making up to 100 mL in ethanol. A stock solution of hexyl resorcinol was prepared at 0.5% in ethanol and then a 1:10 dilution was made in sterile distilled water to achieve a 0.05% stock of Hexyl resorcinol.
Assay Protocol:

The malodour assay was adapted from the method of Moore et al, 2003 and modified into a 96 well plate format. 100 ml Tryptic Soy Broth (TSB) with 0.1% L-cysteine-HCl was added into the wells of the 96-well plate. 20 ml of 0.2 OD culture of *S. hominis* was then added into the wells. The actives were added from the stock solutions at required concentrations and made up the volume to 200 ml with addition of sterile distilled water. The assay was done in triplicates. The lead acetate paper was placed over the wells and the lid of the 96-well plate was closed and incubated at 37° C. incubator overnight. After the incubation time, the dark coloration of the lead acetate paper was observed. Visible blackening of lead acetate in the area over the well indicated the presence of $H_2S$. The intensity of the colour was recorded using a reflectometer as L*a*b* values.

The difference between the initial and final L*a*b* values $\Delta E$, was used to quantify malodour formation.)

$$\Delta E = \sqrt{(L_i - L_f)^2 + (a_i - a_f)^2 + (b_i - b_f)^2}$$

The percentage malodour was calculated from $\Delta E$ measured using the above assay for the various actives or combinations. The results are summarised in the Table—1 below:

TABLE 1

| Example | Active (wt %) | Malodour generation (%) | Std Dev |
|---|---|---|---|
| A | Control | 100 | — |
| B | Hexyl resorcinol (0.0005%) | 96 | 0.04 |
| C | Hexyl resorcinol (0.001%) | 96 | 0.11 |
| D | Thymol (0.005%) + Terpineol (0.005%) | 78 | 0.04 |
| 1 | Hexyl resorcinol (0.001%) + Thymol (0.005%) + Terpineol (0.005%) | 21 | 1.50 |

The data in the above table indicates that the composition according to the present invention (Example—1) is synergistic over the individual values delivered by hexyl resorcinol alone or a combination of thymol and terpineol alone (Examples C and D).

The invention claimed is:

1. An antimicrobial composition comprising:
   i) from 0.0005% to 2% by weight of hexyl resorcinol;
   ii) 0.005% to 1% by weight of the composition of an essential oil compound comprising a combination of thymol and terpineol, and
   iii) a cosmetically acceptable base, wherein the cosmetically acceptable base is selected from an anhydrous base, gel, emulsion, lotion, paste, spray, cream, or any combination thereof,
   wherein the anhydrous base comprises at least one of a silicone compound, an alcohol, or a wax, and
   wherein the composition is a leave-on product selected from a toner, lotion, cream, mousse, serum or gel.

2. The composition according to claim 1, wherein the cosmetically acceptable base is anhydrous.

3. The composition according to claim 1, wherein the composition is in the form of a stick, a roll-on device, or an aerosol can.

4. The composition according to claim 2, wherein the cosmetically acceptable base is in the form of a sanitizer comprising more than 60 wt. % ethanol.

5. The composition according to claim 1 for providing malodor reduction to skin on application of the composition to a skin surface.

6. The composition according to claim 1 for providing anti acne benefit on application of the composition to a skin surface.

7. The composition according to claim 1, wherein the composition is free of fragrance.

8. An antimicrobial composition comprising:
   i) from 0.0005% to 0.001% by weight of hexyl resorcinol;
   ii) 0.005% to 1% by weight of the composition of an essential oil compound consisting of a combination of thymol and terpineol, and
   iii) a cosmetically acceptable base, wherein the cosmetically acceptable base is selected from an anhydrous base, gel, emulsion, lotion, paste, spray, cream, or any combination thereof,
   wherein the anhydrous base comprises at least one of a silicone compound, an alcohol, or a wax;
   wherein the composition is a leave-on product selected from a toner, lotion, cream, mousse, serum or gel; and
   wherein the composition is free of fragrance.

* * * * *